US012779088B2

(12) United States Patent
Shigemura et al.

(10) Patent No.: US 12,779,088 B2
(45) Date of Patent: Nov. 3, 2026

(54) AGENT FOR SUPPRESSING ADHESION OF CALCULI OR CALCIFICATION IN MEDICAL DEVICE, MEDICAL DEVICE LESS SUSCEPTIBLE TO ADHESION OF CALCULI OR CALCIFICATION, AND METHOD FOR MANUFACTURING MEDICAL DEVICE LESS SUSCEPTIBLE TO ADHESION OF CALCULI OR CALCIFICATION

(71) Applicant: NATIONAL UNIVERSITY CORPORATION KOBE UNIVERSITY, Kobe (JP)

(72) Inventors: Katsumi Shigemura, Kobe (JP); Hideto Matsuyama, Kobe (JP); Kazuo Kumagai, Kobe (JP); Youngmin Yang, Kobe (JP)

(73) Assignee: National University Corporation Kobe University, Kobe (JP)

( * ) Notice: Subject to any disclaimer, the term of this patent is extended or adjusted under 35 U.S.C. 154(b) by 509 days.

(21) Appl. No.: 18/547,115

(22) PCT Filed: Feb. 15, 2022

(86) PCT No.: PCT/JP2022/005850
§ 371 (c)(1),
(2) Date: Aug. 18, 2023

(87) PCT Pub. No.: WO2022/176834
PCT Pub. Date: Aug. 25, 2022

(65) Prior Publication Data
US 2024/0157028 A1 May 16, 2024

(30) Foreign Application Priority Data
Feb. 19, 2021 (JP) ................................ 2021-025274

(51) Int. Cl.
*A61L 27/34* (2006.01)
*A61L 27/50* (2006.01)
(Continued)

(52) U.S. Cl.
CPC ............... *A61L 27/34* (2013.01); *A61L 27/50* (2013.01); *A61L 29/085* (2013.01); *A61L 31/10* (2013.01);
(Continued)

(58) Field of Classification Search
CPC .......... A61L 27/28; A61L 27/34; A61L 27/50; A61L 27/507; A61L 29/08; A61L 29/085;
(Continued)

(56) References Cited

PUBLICATIONS

International Search Report received in International Application No. PCT/JP2022/005850 mailed May 17, 2022.
(Continued)

*Primary Examiner* — Robert A Lynch
(74) *Attorney, Agent, or Firm* — Knobbe, Martens, Olson & Bear, LLP

(57) ABSTRACT

Provided is a technology that can provide an excellent suppressive effect against adhesion of calculi or calcification in a medical device to be retained within the body. This agent for suppressing calculi adhesion or calcification contains polydopamine and/or a derivative thereof, and is used to form at least an outermost surface of a coating layer of a medical device to be retained within a urinary organ or a circulatory organ.

7 Claims, 3 Drawing Sheets

(51) Int. Cl.
*A61L 29/08* (2006.01)
*A61L 31/10* (2006.01)

(52) U.S. Cl.
CPC ....... *A61L 2400/02* (2013.01); *A61L 2420/00* (2013.01)

(58) Field of Classification Search
CPC ...... A61L 31/08; A61L 31/10; A61L 2400/00; A61L 2400/02; A61L 2420/00; A61L 2420/02
See application file for complete search history.

(56) References Cited

PUBLICATIONS

Fan, Y.-J. et al., "Development of Antimicrobial and Antifouling Universal Coating via Rapid Deposition of Polydopamine and Zwitterionization". Langmuir. 2019. 35(5). 1642-1651.
Hertault, A. et al., "In vivo evaluation of a pro-healing polydopamine coated stent through an in-stent restenosis rat model". Biomater Sci., Jan. 5, 2021. 9(1). 212-220.
Su, L. et al., "Strong Antibacterial Polydopamine Coatings Prepared by a Shaking-assisted Method". Scientific Reports. 2016. 6(1): 24420 (in 8 pages).
Matsuzaki, J., Jpn J Endourol. 2018. 31. 201-206. non-official translation (Complications of ureteral stent.).
Japanese Journal of Endourology, "Ureteral stent complications" (2014) 27: 71-78.
Matsumoto, H. et al. "Distribution Dynamics of Ca in transplanted artificial vessel fragments from EDX analysis", Jpn J Artif Organs, 18 (1). (1989), 261-263.
Kawamura et al., "Polydopamine-Assisted Surface Modification and Optical Application", Surface Technology (2017), vol. 68, No. 3, 138-142.
Written Opinion of the International Searching Authority in International Application No. PCT/JP2022/005850, dated May 17, 2022.

AGENT FOR SUPPRESSING ADHESION OF CALCULI OR CALCIFICATION IN MEDICAL DEVICE, MEDICAL DEVICE LESS SUSCEPTIBLE TO ADHESION OF CALCULI OR CALCIFICATION, AND METHOD FOR MANUFACTURING MEDICAL DEVICE LESS SUSCEPTIBLE TO ADHESION OF CALCULI OR CALCIFICATION

TECHNICAL FIELD

The present invention relates to an agent for suppressing adhesion of calculi or calcification in a medical device, a medical device less susceptible to adhesion of calculi or calcification, and a method for manufacturing a medical device less susceptible to adhesion of calculi or calcification

BACKGROUND ART

In the urological field, a treatment of retaining a stent or a catheter in a ureter, a renal pelvis, a bladder, or the like may be performed. In addition, replacement with an artificial blood vessel or bypass treatment may be performed in the circulatory system field. Such a medical device retained in the body, such as a stent, a catheter, or an artificial blood vessel, is made of an artificial material, and therefore continuous contact with a body fluid in a living body causes deposition of an insoluble substance such as adhesion of calculi or calcification. Such deposition not only hinders long-term use of the medical device, but the greater the degree of deposition, the higher the risk of complications by causing blockage of the device, the more complex the treatment to be applied, and the more invasive the patient at the time of removal and replacement. In particular, if a ureteral stent is occluded due to adhesion of calculi, it can cause pain, deterioration of renal function, infection, and the like in a patient, and in some cases, death is caused from sepsis in severe cases. Therefore, it is necessary to frequently remove and replace the stent.

The cause of calculi formation on the ureteral stent has not been completely elucidated, but different mechanisms have been reported depending on the presence or absence of infection in the urine. The mechanism of adhesion of calculi to the ureteral stent in infected urine is thought to be that organic components such as uric acid in urine are crystallized on the surface of the stent, incorporated into a biofilm layer of bacteria and decomposed to produce ammonia, resulting in pH increase of urine which induces crystallization and deposition of magnesium and calcium salts (Non-Patent Document 1). In addition, the mechanism of adhesion of calculi to the ureteral stent in the urine without infection is also unknown, but is speculated to be related to urine pH, urinary ionic strength, and hydrophobicity of the stent material (Non-Patent Document 1). At this time, the calculi adhering to the ureteral stent are often calcium oxalate.

The mechanism of calcification on artificial blood vessels is considered that calcium phosphate hydroxyapatite is deposited and grows on the surface using necrotic and degenerated cells as nuclei, regardless of the difference in materials (Non-Patent Document 2).

Meanwhile, in recent years, a surface modification technology using polydopamine (hereinafter, also referred to as "PDA") has been studied. PDA is a catechol-based biomimetic adhesion polymer designed to imitate the amino acid dopa which is characterized by a catechol group that involves in the adhesion mechanism of seashells (Non- Patent Document 3). Since PDA has many catechol groups, amino groups, and benzene rings in its structure, it can bind to hydrophilic resin materials, inorganic materials, metallic materials, hydrophobic resin materials, or the like regardless of material (Non-Patent Document 3). In particular, since the catechol groups in PDA have metal-binding ability, PDA is also actively used for metal surface modification by taking advantage of its metal-complexing properties (Non-Patent Document 3).

PDA can be obtained by self-oxidative polymerization of dopamine (DA), but its polymerization mechanism is very complicated, and many studies are still in progress. While PDA has been thought to be a covalently linked polymer of 5,6-dihydroxyindole (DHI) generated by the oxidation of DA, it has also been reported that DHI or its derivatives may form supramolecular aggregates through physical bonding, and at present, the structure combining these two mechanisms is widely supported (Non-Patent Document 3). That is, it is considered that PDA is not a polymer having a clear single structure, but a structure in which molecular chains are three-dimensionally extended by covalent bonds and a structure due to non-covalent physical interactions coexist (Non-Patent Document 3).

PRIOR ART DOCUMENTS

Patent Documents

Non-Patent Document 1: Japanese Journal of Endourology (2014) 27: 71-78

Non-Patent Document 2: Artificial Organs 18 (1), 261-263 (1989)

Non-Patent Document 3: The Journal of the Surface Finishing Society of Japan Vol. 68, No. 3, 138-142 (2017)

SUMMARY OF THE INVENTION

Problems to be Solved by the Invention

For the purpose of suppressing adhesion of calculi or calcification to a medical device that is to be retained in the body, surface modifications or the like by hydrophilic treatment based on the mechanisms of the adhesion of calculi or calcification have been conducted, but the suppression property against the adhesion of calculi or calcification is still insufficient.

The object of the present invention is to provide a technology that can impart an excellent suppressive effect against adhesion of calculi or calcification in a medical device to be retained in the body.

Means for Solving the Problem

As a result of intensive studies, the present inventors have found that PDA, which has not been used for surface coating of a medical device to be retained in the body, can exhibit an excellent suppression property against adhesion of calculi and calcification. In view of the adhesion properties (metal bonding ability, and the like), which are the most characteristic properties of PDA, it was unexpected that such an excellent effect was obtained by using PDA, which has been supposed to be the least suitable material for the coating. The present invention has been completed by further studies based on this finding.

That is, the present invention provides inventions of the following aspects.

Item 1. An agent for suppressing adhesion of calculi or calcification containing polydopamine and/or a derivative thereof, wherein the agent for suppressing adhesion of calculi or calcification is used to form at least an outermost surface of a coating layer of a medical device to be retained within a urinary organ or a circulatory organ.

Item 2. The agent for suppressing adhesion of calculi or calcification according to item 1, wherein the polydopamine and/or the derivative thereof is obtained by a reacting for 1 to 5 days in a reaction solution of pH 8.3 to 10 containing dopamine and/or a derivative thereof at a concentration of 5 to 16 mM.

Item 3. The agent for suppressing adhesion of calculi or calcification according to item 1 or 2, wherein the medical device is a ureteral stent, a renal pelvis catheter, a urethral catheter, or an artificial blood vessel.

Item 4. A medical device less susceptible to adhesion of calculi or calcification, the medical device comprising: a medical device to be retained in a urinary organ or a circulatory organ; and a coating layer provided on a surface of the medical device, wherein at least an outermost surface of the coating layer is a layer containing polydopamine and/or a derivative thereof.

Item 5. A method for manufacturing a medical device less susceptible to adhesion of calculi or calcification, the method comprising: a step of reacting for 1 to 5 days in a reaction solution of pH 8.3 to 10 containing dopamine and/or a derivative thereof at a concentration of 5 to 16 mM in which a medical device to be retained in a urinary organ or a circulatory organ is immersed, thereby forming a layer containing polydopamine and/or a derivative thereof on a surface of the medical device, wherein the method does not include a step of further providing other layer on the surface of the layer.

Advantages of the Invention

According to the present invention, there is provided a technology that can impart an excellent suppressive effect against adhesion of calculi or calcification in a medical device to be retained in the body.

EMBODIMENTS OF THE INVENTION

Figure 1:
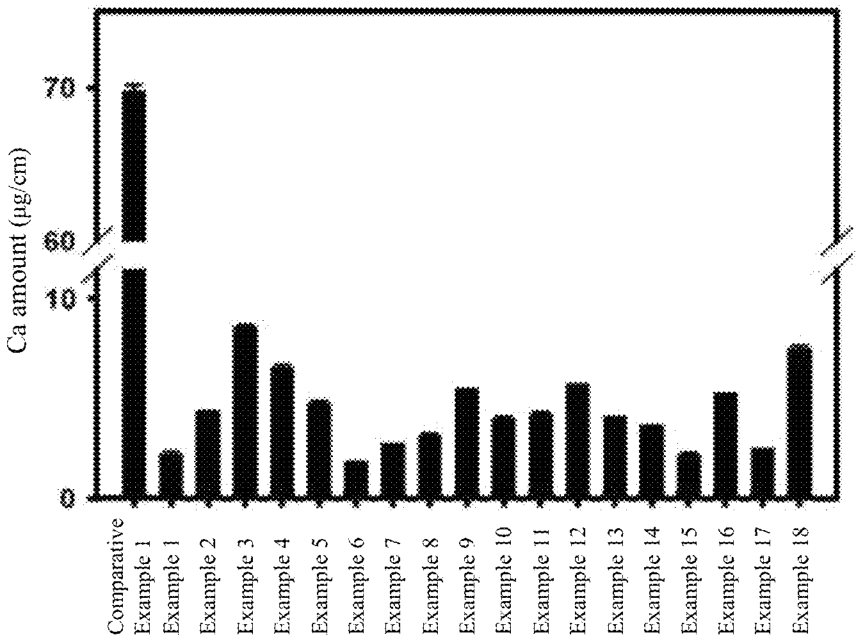
FIG. 1 is a graph obtained in Test Example 1, showing comparison of the adhesion amounts of calcium oxalate crystals (calculi components) to a ureteral stent not coated with polydopamine (Comparative Example 1) and a ureteral stent coated with polydopamine (Examples 1 to 18).

1. Agent for Suppressing Adhesion of Calculi or Calcification

An agent for suppressing adhesion of calculi or calcification of the present invention is characterized by containing polydopamine and/or a derivative thereof, and used to form at least an outermost surface of a coating layer of a medical device to be retained in a urinary organ or a circulatory organ. Hereinafter, the agent for suppressing adhesion of calculi or calcification of the present invention will be described in detail.

1-1. Polydopamine and/or a Derivative Thereof

Polydopamine is an oxidized polymer of dopamine.

The derivative of polydopamine is an oxidized polymer of a dopamine derivative, and/or an oxidized polymer of dopamine and a dopamine derivative. The dopamine derivative is a compound in which a substituent is introduced into dopamine. Examples of the derivative of polydopamine used in the present invention include an oxidized polymer of dopamine derivative represented by the following general formula (1).

[Chemical Formula 1]

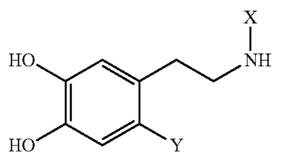

(1)

In the general formula (1), X represents a hydrogen atom, a hydroxyl group, an alkyl group having 1 to 5 carbon atoms, an alkoxyl group having 1 to 5 carbon atoms, a halogen atom, a polymerization initiating group, a sugar group, or a dye group. In the general formula (1), Y represents a hydrogen atom, a hydroxyl group, an alkyl group having 1 to 5 carbon atoms, an alkoxyl group having 1 to 5 carbon atoms, a halogen atom, a polymerization initiating group, a sugar group, or a dye group. Note that, in the general formula (1), both X and Y do not represent a hydrogen atom.

Dopamine and/or derivatives thereof used for the formation of polydopamine and/or a derivative thereof may be in the form of salts, such as hydrochloride salt, as long as they are oxidative polymerizable.

In the present invention, polydopamine and a derivative thereof may be a polymer containing a constituent unit derived from other comonomer in addition to the dopamine and/or a dopamine derivative, as long as the suppressive effect on adhesion of calculi or calcification of the present invention is exhibited. From the viewpoint of further improving the suppressive effect on adhesion of calculi or calcification, it is preferable that polydopamine and a derivative thereof are polymers containing only a constituent unit derived from dopamine and/or a dopamine derivative without containing a constituent unit derived from other comonomer.

In the present invention, one polymer may be selected from the polydopamine and derivatives thereof and used alone, or two or more polymers may be used in combination. Among polydopamine and derivatives thereof, polydopamine is preferable.

The polydopamine is not particularly limited as long as that is a polymer obtained by oxidatively polymerizing dopamine and/or a derivative thereof under basic conditions, and examples thereof include a polymer obtained by reacting dopamine and/or a derivative thereof for 1 to 5 days in a reaction solution of pH 8.3 to 10 (22° C.) containing dopamine and/or a derivative thereof at a total concentration of 5 to 16 mM. From the viewpoint of further improving the suppressive effect on adhesion of calculi or calcification, the total concentration of dopamine and/or a derivative thereof subjected to the above reaction is preferably 8 to 16 mM, more preferably 10 to 16 mM, even more preferably 10.2 to 14 mM, still more preferably 10.4 to 12 mM, yet more preferably 10.4 to 11 mM, and particularly preferably 10.4 to 10.8 mM; the pH (22° C.) is preferably 8.5 to 9.5, and more preferably 8.7 to 9.3; the reaction time is preferably 2 to 4 days, more preferably 2.5 to 3.5 days, even more preferably 65 to 80 hours, and still more preferably 70 to 75 hours. The reaction temperature may be an ordinary temperature, and is, for example, 15° C. to 25° C., and is preferably 18° C. to 24° C. and more preferably 20° C. to 23° C. from the viewpoint of further improving the suppression property against the adhesion of calculi or calcification.

In the agent for suppressing adhesion of calculi or calcification of the present invention, the hydrophilicity of a layer surface when formed as a layer is preferably 85° or less, more preferably 80° or less, even more preferably 75° or less, and still more preferably 73° or less as the contact angle of the layer surface to water (the contact angle at 1 second after the droplet of water is deposited) from the viewpoint of further improving the suppression property against the adhesion of calculi or calcification. The lower limit of the range of the contact angle is not particularly limited, and is preferably as small as possible, but is, for example, 65° or more, or 68° or more.

1-2. Application

The agent for suppressing adhesion of calculi or calcification of the present invention is used for the purpose of modifying the surface of a medical device to be retained in a urinary organ or a circulatory organ so as to suppress adhesion of calculi or calcification. Specific examples of the adhesion of calculi or calcification to be suppressed include the adhesion of calculi observed on the surface of the medical device retained in the urinary organ and the calcification observed on the surface of the medical device retained in the circulatory organ. Examples of the component constituting calculi or a calcified substance include calcium compounds such as calcium oxalate and calcium phosphate, and magnesium compounds.

An example of the medical device is not particularly limited as long as it is to be retained in a urinary organ or a circulatory organ. The present invention is excellent in the suppressive effect on the adhesion of calculi or calcification and therefore the present invention is highly useful when used for a device having a shape that may cause blockage by calculi or a calcified substance, such as an elongated shape with narrow hollow space, specifically tube shape. From such a viewpoint, preferable examples of the medical device include a ureteral stent, a renal pelvis catheter, a urethral catheter, and an artificial blood vessel. Among these, a particularly preferable example of the medical device includes a ureteral stent, which has especially high degree and frequency of calculi adhesion.

The agent for suppressing adhesion of calculi or calcification of the present invention is used so as to constitute at least the outermost surface of the coating layer of the medical device. The outermost surface means a surface that comes into contact with a body fluid when the medical device is retained in the body. For example, when used in the tube shaped medical device, the outermost surface corresponds to the outermost surface of the coating layer at least on the inner peripheral side of the tube (for example, only the inner peripheral side, or both the inner peripheral side and the outer peripheral side).

The coating layer may be composed of a layer of the agent for suppressing adhesion of calculi or calcification of the present invention, or may be composed of a multilayer including a layer composed of the agent for suppressing adhesion of calculi or calcification of the present invention and one or more other layer(s). If the coating layer is composed of multilayers, the outermost layer (that is, the layer constituting the outermost surface) of the constituent layers of the multilayer corresponds to a layer formed of the agent for suppressing adhesion of calculi or calcification of the present invention. The layer composed of the agent for suppressing adhesion of calculi or calcification of the present invention is preferably a layer obtained by immersing the medical device (specifically, the medical device itself or a medical device having a surface coated with other layer in advance) in the reaction solution described in the above item 1-1, whereby an oxidative polymerization reaction is performed on the surface of the medical device to form the layer.

The material constituting the medical device is not particularly limited, and widely includes resins and metals used in known medical devices. Preferably, examples of the materials include resins such as an ethylene-vinyl acetate copolymer resin, a silicone resin, a polyurethane resin, and a polyethylene terephthalate resin. Regarding the medical device in which the above-described surface is coated with other layer in advance, the other layer coated in advance is not particularly limited, and may include, for example, any of a layer provided for the purpose of improving adhesion of the layer composed of the agent for suppressing adhesion of calculi or calcification of the present invention, a layer provided for the purpose of improving the effect of suppressing adhesion of calculi or calcification, and a layer already provided for surface modification in a known medical device (for example, a hydrophilic layer or the like).

2. Medical Device Less Susceptible to Adhesion of Calculi or Calcification and Method for Manufacturing the Same As described above, the agent for suppressing adhesion of calculi or calcification of the present invention exerts an excellent suppressive effect on adhesion of calculi or calcification when coated on the surface of the medical device. Therefore, the present invention also provides a medical device less susceptible to adhesion of calculi or calcification with the agent for suppressing adhesion of calculi or calcification of the present invention, and a method for manufacturing the same.

Specifically, the medical device less susceptible to adhesion of calculi or calcification of the present invention is characterized by including a medical device to be retained in a urinary organ or a circulatory organ, and a coating layer provided on a surface of the medical device, wherein at least the outermost surface of the coating layer is a layer containing polydopamine and/or a derivative thereof. A method for manufacturing the medical device less susceptible to adhesion of calculi or calcification of the present invention is characterized by including a step of reacting for 1 to 5 days in a reaction solution of pH 8.3 to 10 (22° C.) containing dopamine and/or a derivative thereof at a concentration of 5 to 16 mM in which a medical device to be retained in a urinary organ or a circulatory organ is immersed, thereby forming a layer containing polydopamine and/or a derivative thereof on a surface of the medical device, and not including a step of further providing other layer on the surface of the layer.

In the medical device less susceptible to adhesion of calculi or calcification of the present invention and the method for manufacturing the same, the conditions and specific examples as well as preferable examples for "medical device", "coating layer", "polydopamine and/or a derivative thereof", "dopamine and/or a derivative thereof", "reaction solution", and "reaction" are as described above in "1. Agent for suppressing adhesion of calculi or calcification".

EXAMPLES

Hereinafter, the present invention will be described in detail based on examples, but the present invention is not limited thereto.

Test Example 1

(1) Manufacture of Ureteral Stent Coated with Polydopamine

As a ureteral stent, Percuflex™ Urinary Diversion Stent Open Tip 6F×80 cm (Boston Scientific Corporation, made of ethylene-vinyl acetate copolymer resin) was used. Dopamine hydrochloride (Sigma-Aldrich, H8502) was dissolved in a 10 mM Tris buffer solution (pH (22° C.) was adjusted to the pH shown in Table 1 using 0.2 M aqueous HCl or 0.2 M aqueous NaOH) at a concentration shown in Table 1, then 15 ml of the solution was placed in a 50 ml glass vial, and the ureteral stent cut into 1 to 2 cm was immersed. The vial was capped and subjected to oxidative polymerization by reacting for the time period shown in Table 1 while rotationally shaking at 80 rpm at room temperature (about 22° C.) to form a layer composed of polydopamine on the surface of the ureteral stent. After the reaction, the ureteral stent was taken out and washed by immersion three times using pure water. After washing the ureteral stent was kept in pure water and subjected within 3 days to an evaluation test for the effect on suppression of adhesion of calculi or calcification

TABLE 1

| | pH (22° C.) | Dopamine hydrochloride concentration (mM) | Reaction time (days) |
|---|---|---|---|
| Comparative Example 1 | Not coated with polydopamine | | |
| Example 1 | 8.5 | 15.8 | 3 |
| Example 2 | 8.5 | 15.8 | 1 |
| Example 3 | 8.5 | 5.3 | 1 |
| Example 4 | 8.5 | 5.3 | 3 |
| Example 5 | 8.5 | 10.5 | 2 |
| Example 6 | 9 | 10.5 | 3 |
| Example 7 | 9 | 15.8 | 2 |
| Example 8 | 9 | 10.5 | 1 |
| Example 9 | 9 | 5.3 | 2 |
| Example 10 | 8 | 15.8 | 2 |
| Example 11 | 8 | 5.3 | 2 |
| Example 12 | 8 | 10.5 | 1 |
| Example 13 | 8 | 10.5 | 3 |
| Example 14 | 8.5 | 10.5 | 3 |
| Example 15 | 9.5 | 10.5 | 3 |
| Example 16 | 10 | 10.5 | 3 |
| Example 17 | 9 | 10.5 | 4 |
| Example 18 | 9 | 10.5 | 5 |

(2) Measurement of Surface State of Polydopamine Coating Layer

Using the polydopamine-coated ureteral stent of Example 6, the water contact angle of the surface of the polydopamine layer was measured under the following conditions.

The measurement was performed at a temperature of 25° C. and a humidity of 29 to 34% using an automatic contact angle meter (manufactured by Kyowa Interface Science Co., Ltd.: product number Drop Master 300). The automatic contact angle meter consists of a sample mounting stage movable in the vertical direction, a syringe part installed above the sample mounting stage, and a scope part capable of horizontally observing the stage. First, water was aspirated into the syringe, and a polydopamine-coated ureteral stent was fixed to the stage vertically below the syringe. The stage was moved upward, and a droplet of water (0.3 μL) was placed in contact with the polydopamine layer at a point where a tangential plane was horizontal. The curvature of the surface of the polydopamine layer was 0.5 $mm^{-1}$. The contact angle between the water droplet and the polydopamine layer (the contact angle when viewed in the direction parallel to the axis of the ureteral stent; θ) was determined by the θ/2 method at 1 second after the water deposition.

The contact angle of the polydopamine layer measured by the above method was 70.2° on the day 1 of the manufacture of the polydopamine-coated ureteral stent. The contact angle of the polydopamine layer remained stable at 70.2° even on the day 90 after the manufacture of the polydopamine-coated ureteral stent.

(3) Evaluation Test on Suppression of Adhesion of Calculi or Calcification

A $CaCl_2$ solution was prepared by dissolving $CaCl_2$ in a Tris-NaCl buffer solution (contains 0.05M Tris and 0.15 M NaCl, pH 6.5 (pH value is at 22° C. and adjusted with 0.2 M HCl aqueous solution)) to a concentration of 16 mM and sterilized by filtrating the solution through a membrane filter with a pore size of 0.22 μm. Similarly, 2 mM sodium oxalate solution was prepared. Both solutions were mixed at 1:1 (volume ratio) and adjusted to pH 10 (22° C.) with 5 M NaOH to initiate the formation of calcium oxalate crystals. Two ml of the solution in which calcium oxalate crystals began to form was taken in a microtube, and the ureteral stent obtained in the above (1) was immersed and incubated at 37° C. for 2 weeks. After the incubation, the ureteral stent was taken out, washed with pure water three times, and then immersed in 2 ml of aqueous 2 wt % nitric acid solution for 12 hours to dissolve calcium oxalate crystals adhered to the surface of the ureteral stent. The weight of calcium dissolved in the aqueous nitric acid solution per 1 cm of a ureteral stent (μg/cm) was quantified by elemental analysis using inductively coupled plasma (ICP) atomic emission spectroscopy method (ICPE-9820 manufactured by Shimadzu Corporation was used). The results are illustrated in FIG. 1.

As illustrated in FIG. 1, as compared with the ureteral stent not coated with polydopamine (Comparative Example 1), the ureteral stent coated with polydopamine (Examples 1 to 18) strongly suppressed the adhesion of calcium oxalate crystals. In particular, in Example 6, the adhesion of calcium oxalate crystals was suppressed to 3% of that in Comparative Example 1.

Test Example 2

Figure 2:
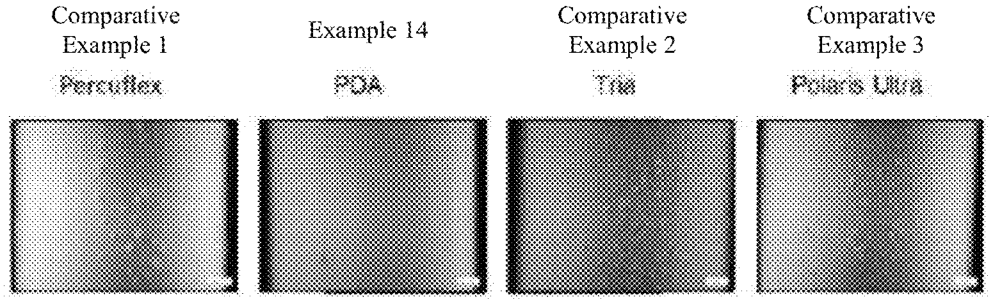
FIG. 2 is a stereomicroscopic photograph obtained in Test Example 2, showing surfaces of commercially available ureteral stents with a surface modification treatment for suppressing adhesion of calculi (Comparative Example 2 and Comparative Example 3) and a polydopamine-coated ureteral stent (Example 14) after an evaluation test regarding suppression of adhesion of calculi or calcification.

The results of the evaluation test regarding suppression of adhesion of calculi or calcification were compared between a commercially available ureteral stent with surface modification for inhibition of adhesion of calculi and the polydopamine-coated ureteral stent of Example 14 prepared in Test Example 1. As commercial ureteral stents, Tria™ (Comparative Example 2) manufactured by Boston Scientific Corporation with surface smoothing treatment and without a hydrophilic coating, and Polaris™ Ultra (Comparative Example 3) manufactured by Boston Scientific Corporation with surface hydrophilization treatment were used. The evaluation test regarding suppression of adhesion of calculi or calcification was performed in the same manner as in the method shown in (3) of Test Example 1 except that the period of immersing the ureteral stent was set to one week. FIG. 2 shows a photograph taken by a stereomicroscope of the surface after the evaluation test regarding suppression of adhesion of calculi or calcification. FIG. 2 also shows the result of similar evaluation of Comparative Example 1, in which the surface modification treatment is not performed.

As shown in FIG. 2, in the commercial ureteral stent products (Comparative Example 2 and Comparative Example 3) with surface modification treatment for inhibition of adhesion of calculi, the size of the adhered calculi was smaller than that in Comparative Example 1, and a slight suppressive effect against adhesion of calculi was observed. However, in the polydopamine-coated ureteral stent (Example 14), it was observed that adhesion of calculi was remarkably suppressed as compared with Comparative Example 2 and Comparative Example 3.

Figure 3:
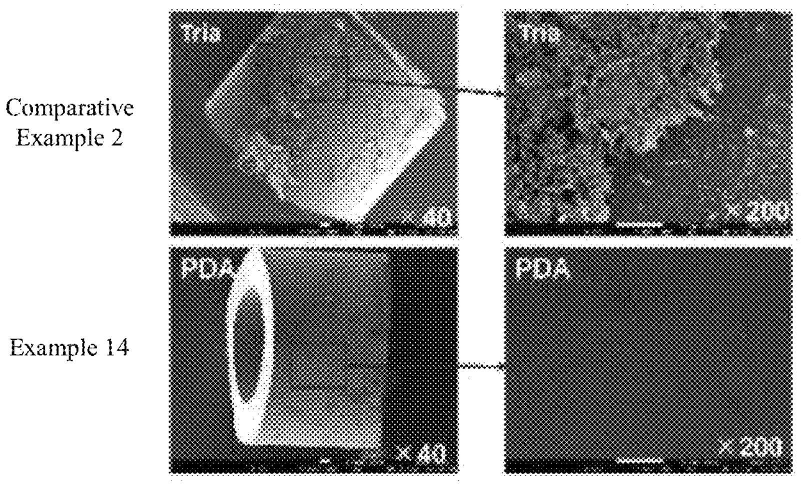
FIG. 3 is an image observed with a field emission scanning electron microscope (40× magnification and 200× magnification) obtained in Test Example 2, showing the surfaces of the ureteral stents of Comparative Example 2 and Example 14 after the evaluation test regarding the suppression of adhesion of calculi or calcification.

FIG. 3 shows images obtained by observing the surface of the ureteral stent with a field emission scanning electron microscope (40× magnification and 200× magnification) after the evaluation test regarding the suppression of adhesion of calculi or calcification according to Comparative Example 2 and Example 14. As is clear from FIG. 3, it was observed that adhesion of calculi was remarkably suppressed in the polydopamine-coated ureteral stent (Example 14).

Test Example 3

Figure 4:
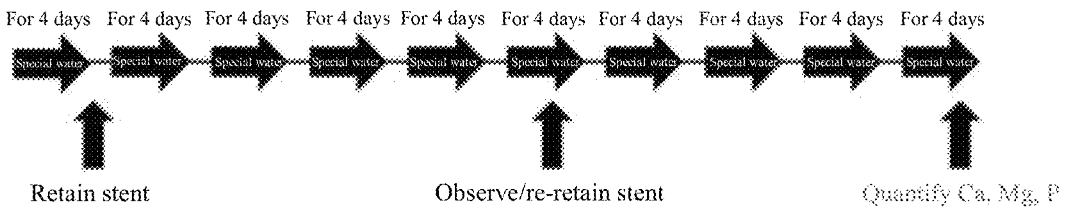
FIG. 4 illustrates a test schedule of Test Example 3.

Fifteen male SD rats were prepared and tested according to the schedule illustrated in FIG. 4. An aqueous solution containing 4 wt % ethylene glycol and 1 wt % ammonium chloride in water was freely taken as special water for 4 days. On the fifth day after the start of drinking the special water, rats were divided into three groups, and surgery was performed, for each group, in which the ureteral stent of Comparative Example 1, Example 6 or Comparative Example 2 was retained in the bladder. After the surgery, as illustrated in FIG. 4, the special water was freely taken at a frequency of 4 days/week, and the stent was once taken out at week 5 and observed with a stereomicroscope. After the observation, the stent was immediately re-retained in the bladder, and free drinking of the special water was continued again at a frequency of 4 days/week, and the ureteral stent was removed at week 9 from the day on which the stent was first retained.

Figure 5:
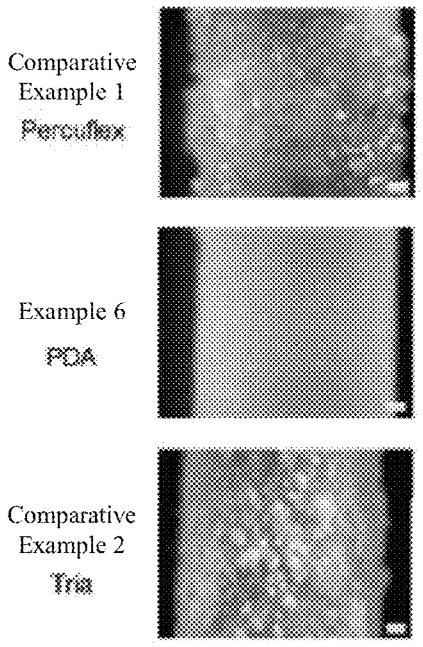
FIG. 5 is a photograph obtained in Test Example 3, showing surfaces of ureteral stents of Comparative Example 1, Example 6, and Comparative Example 2, which were removed after being retained in a rat bladder for four weeks.

When the surface of the stent retained in the rat bladder for 4 weeks was observed with a stereomicroscope, it was confirmed that adhesion of calculi was remarkably suppressed in Example 6. As representative examples of Comparative Example 1, Example 6, and Comparative Example 2, photographs obtained by photographing the surface of the ureteral stent are shown in FIG. 5. As shown in FIG. 5, in the commercially available ureteral stent (Comparative Example 2) with surface modification treatment for inhibition of adhesion of calculi, the adhered calculi were smaller than that in Comparative Example 1, and a slight suppressive effect against adhesion of calculi was observed. However, in the polydopamine-coated ureteral stent (Example 6), it was observed that adhesion of calculi was remarkably suppressed as compared with Comparative Example 2.

Test Example 4

Components of calculi adhered to the ureteral stents of Comparative Example 1 and Example 6 retained in the rat bladder for 8 weeks in Test Example 3 were analyzed and quantified. Specifically, the ureteral stent removed from the rat bladder was gently washed three times in pure water, and then dried at 50° C. for 24 hours. This was immersed in 10 ml of 1 wt % nitric acid and left at room temperature for 3 days, and then the calculi component was completely dissolved using an ultrasonic bath. The amounts of calcium, magnesium, and phosphorus (main components of urinary calculi) in this solution were quantified by elemental analysis with inductively coupled plasma (ICP) emission spectrophotometry (using ICPE-9820 manufactured by Shimadzu Corporation). The quantitative results of the weight of each element per 1 cm of the ureteral stent (mg/cm) are shown in FIG. 6.

Figure 6:
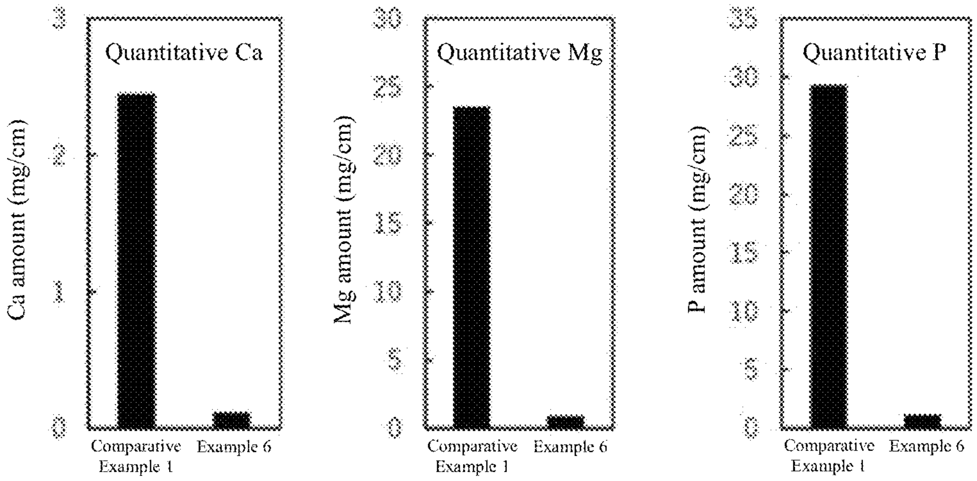
FIG. 6 is an analysis result obtained in Test Example 4, showing components of calculi adhered to the surfaces of ureteral stents of Comparative Example 1 and Example 6, which were removed after being retained in the rat bladder.

As shown in FIG. 6, in the polydopamine-coated ureteral stent (Example 6), the adhesion amount of any of calcium, magnesium, and phosphorus was suppressed to less than 10% as compared with the ureteral stent of Comparative Example 1 without the coating.

Test Example 5

The following medical devices were subjected to an evaluation test regarding suppression of adhesion of calculi or calcification. The medical devices used in the present test example are an artificial blood vessel for bypass (Mini-Shunt Pro No. 9, made of silicone resin, manufactured by Fuji Systems) and a urethral catheter (All Silicone Foley Catheter, 16 Fr, 5 mL, made of silicone resin, manufactured by CREATE MEDIC CO., LTD.). Each of the artificial blood vessel and the urethral catheter was coated with polydopamine under the same conditions as in Example 6. For the polydopamine-coated artificial blood vessel (Example 19) and the artificial blood vessel not coated with polydopamine (Comparative Example 4), and the polydopamine-coated urethral catheter (Example 20) and the urethral catheter not coated with polydopamine (Comparative Example 5), an evaluation test regarding suppression of adhesion of calculi or calcification was performed in the same manner as in (3) of Test Example 1, and the calcium weight per 1 cm of the artificial blood vessel or the urethral catheter (μg/cm) was quantified. The results are shown in FIG. 7.

Figure 7:
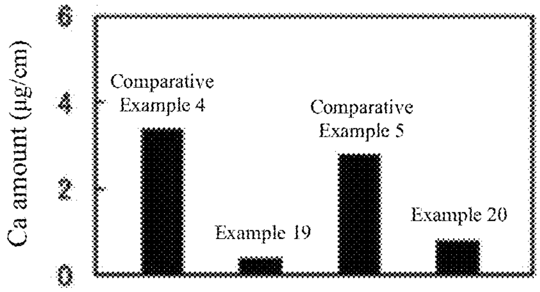
FIG. 7 is a graph obtained in Test Example 5, showing comparison of the amounts of calcium oxalate crystals (calculi components) adhered to an artificial blood vessel and a urethral catheter not coated with polydopamine (Comparative Examples 4 and 5) and that adhered to the artificial blood vessel and the urethral catheter coated with polydopamine (Examples 19 and 20).

As shown in FIG. 7, the comparison between Comparative Example 4 and Example 19 showed that calcification of the artificial blood vessel was also significantly suppressed by polydopamine coating. The comparison between Comparative Example 5 and Example 20 showed that adhesion of calculi for the urethral catheter was also remarkably suppressed by polydopamine coating.

Test Example 6

In this test example, the adhesion suppressive effect was compared between a ureteral stent coated with polyvinyl alcohol which exhibits a contact angle similar to that of polydopamine coating and a ureteral stent coated with polydopamine.

One mL of polyvinyl alcohol (Molecular weight: 89,000 to 98,000, manufactured by Sigma-Aldrich Co. LLC) and 99 mL of pure water were mixed, stirred at 95° C. for 6 hours to be dissolved, and further held at 60° C. overnight to prepare a 1% polyvinyl alcohol aqueous solution. On the other hand, 1.88 mL of a 25% glutaraldehyde aqueous solution (manufactured by Sigma-Aldrich Co. LLC) and 200 μL of 32% HCl were added to a mixed solution of acetone and pure water in a volume ratio of 1:1, and the mixture was stirred at room temperature for 1 hour to prepare a 50 mM glutaraldehyde acidic aqueous solution. A ureteral stent cut into a length of 1 cm (the same as the commercially available ureteral stent used in Comparative Example 1) was immersed in 100 mL of a 1% polyvinyl alcohol aqueous solution, held at 60° C. for 1 hour, and then the ureteral stent was taken out and placed on filter paper to absorb and remove the liquid. The ureteral stent was immersed in 100 mL of a 50 mM glutaraldehyde acidic aqueous solution, held at room temperature for 1 hour, then taken out, placed on a glass dish, and heated in a thermostatic dryer at 100° C. for 10 minutes to fix the polyvinyl alcohol coating on the ureteral stent. This was washed five times with pure water to obtain a polyvinyl alcohol-coated ureteral stent (Comparative Example 6).

The water contact angle of each of the polyvinyl alcohol-coated ureteral stent of Comparative Example 6, the polydopamine-coated ureteral stent of Example 6, and the ureteral stent of Comparative Example 1 prepared above was measured in the same manner as in Test Example 1 (2). In addition, the suppressive effect on adhesion of calculi was also measured by the same method as in Test Example 1 (3). The results are shown in Table 2.

TABLE 2

| | Stent coated layer | Water contact angle | Ca amount (μg/cm) | Ca calculi suppressing rate |
|---|---|---|---|---|
| Comparative Example 1 | None | 130.4° | 63.8 | — |
| Comparative Example 6 | Polyvinyl alcohol | 74.9° | 27.5 | 56.9% |
| Example 6 | Polydopamine | 70.0° | 2.3 | 95.8% |

The water contact angle of the polyvinyl alcohol-coated ureteral stent (Comparative Example 6) was 74.9°, which was comparable to the water contact angle of 70.0° of the polydopamine-coated ureteral stent (Example 6), with respect to the water contact angle of 130.4° of the ureteral stent (Comparative Example 1) not subjected to the coating operation. On the other hand, the adhesion amount of calcium calculi was 10 times or more larger in the polyvinyl alcohol-coated ureteral stent (Comparative Example 6) than in the polydopamine-coated ureteral stent (Example 6). Accordingly, it was found that the polydopamine coating and the polyvinyl alcohol coating are comparable in surface hydrophilicity, but the polydopamine coating exhibits a remarkably strong calculi adhesion suppressing action as compared with the polyvinyl alcohol coating.

Test Example 7

In this test example, an in vitro calculi adhesion suppression test in artificial urine was performed.

Artificial urine (105.5 mM sodium chloride, 32.3 mM monosodium dihydrogen phosphate, 3.21 mM trisodium citrate, 3.85 mM magnesium sulfate, 63.7 mM potassium chloride, 5.75 mM calcium chloride, 0.318 mM sodium oxalate, 27.6 mM ammonium chloride, 166.5 mM urea, pH 6.0, each component was filter-sterilized with a membrane filter having a pore size of 0.22 μm, and then mixed) was prepared, and the polydopamine-coated ureteral stent of Example 6 and the ureteral stent of Comparative Example 1 (each 5 fibers having a length of 1 cm) were immersed and allowed to stand at 37° C. for 3 weeks for incubation. After the incubation, the ureteral stent was taken out, and calculi adhering to the ureteral stent were quantified in the same manner as in Test Example 1 (3). The results are illustrated in FIG. 8.

Figure 8:
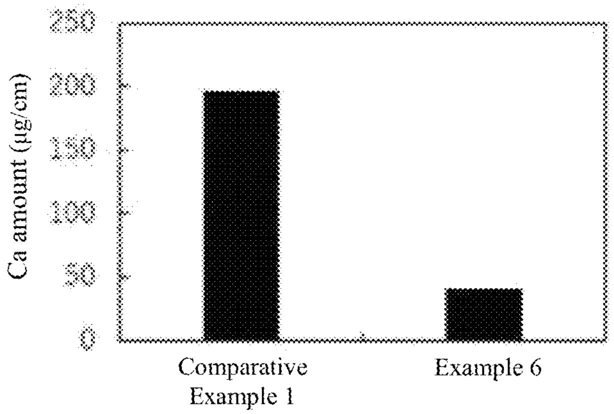
FIG. 8 is a graph obtained in an in vitro calculi adhesion suppression test using artificial urine in Test Example 7, showing comparison of the adhesion amounts of calcium oxalate crystals (calculi component) to a ureteral stent not coated with polydopamine (Comparative Example 1) and a ureteral stent coated with polydopamine (Example 6).

As illustrated in FIG. 8, as compared with the ureteral stent not coated with polydopamine (Comparative Example 1), the ureteral stent coated with polydopamine (Example 6) significantly suppressed adhesion of calcium oxalate calculi in artificial urine.

The invention claimed is:

1. A method of suppressing adhesion of calculi or calcification on a medical device to be retained in a urinary organ or a circulatory organ, the method comprising coating the medical device with a layer of polydopamine and/or a derivative thereof, wherein the coating layer suppresses adhesion of calculi or calcification to at least an outermost surface of the coating layer, wherein the coating layer of polydopamine and/or a derivative thereof is obtained by immersing the medical device for 1 to 5 days in a reaction solution containing dopamine and/or a derivative thereof at a concentration of 5 to 16 mM at a pH of 8.3 to 10.

2. The method of claim 1, wherein the medical device is a ureteral stent, a renal pelvis catheter, a urethral catheter, or an artificial blood vessel.

3. The method of claim 1, wherein the method does not include a step of further providing another layer on the outermost surface of the coating layer.

4. The method according to claim 1, further comprising checking the medical device after a period of time of being retained in a urinary organ or a circulatory organ, wherein adhesion of calculi or calcification on the medical device is suppressed compared to a medical device not coated with the polydopamine and/or a derivative thereof.

5. The method of claim 1, wherein the dopamine and/or a derivative thereof is used at a concentration of 10.4 to 11 mM.

6. The method of claim 1, wherein the pH of the reaction solution is 8.5 to 9.5.

7. The method of claim 1, wherein the reaction time is 2.5 to 3.5 days.

* * * * *